United States Patent [19]

Eggers

[11] Patent Number: 5,496,314
[45] Date of Patent: Mar. 5, 1996

[54] IRRIGATION AND SHROUD ARRANGEMENT FOR ELECTRICALLY POWERED ENDOSCOPIC PROBES

[75] Inventor: Philip E. Eggers, Dublin, Ohio

[73] Assignee: Hemostatic Surgery Corporation, Georgetown, Cayman Islands

[21] Appl. No.: 958,946

[22] Filed: Oct. 9, 1992

Related U.S. Application Data

[63] Continuation-in-part of Ser. No. 877,476, May 1, 1992, abandoned.

[51] Int. Cl.⁶ ..................................................... A61B 17/32
[52] U.S. Cl. ................................. 606/41; 606/29; 606/46; 606/48
[58] Field of Search ........................... 606/28–40, 46, 606/47, 48

[56] References Cited

U.S. PATENT DOCUMENTS

| | | | |
|---|---|---|---|
| Re. 33,644 | 7/1991 | Hall | 219/10.41 |
| 3,662,152 | 5/1972 | Weller | 219/241 |
| 3,987,795 | 10/1976 | Morrison | 606/45 |
| 4,185,632 | 1/1980 | Shaw | 606/45 |
| 4,618,885 | 10/1986 | Nagasaki et al. | 606/46 X |
| 4,622,966 | 11/1986 | Beard | 606/28 |
| 4,657,018 | 4/1987 | Hakky | 606/46 |
| 4,919,129 | 4/1990 | Weber, Jr. et al. | 606/45 |
| 4,936,842 | 6/1990 | D'Amelio et al. | 606/42 |
| 5,013,312 | 5/1991 | Parins et al. | 606/37 |
| 5,080,660 | 1/1992 | Buelna | 606/50 X |
| 5,088,997 | 2/1992 | Delahuerga et al. | 606/45 X |
| 5,151,101 | 9/1992 | Grossi et al. | 606/46 |
| 5,195,958 | 3/1993 | Phillips | 606/45 X |
| 5,201,741 | 4/1993 | Dulebohn | 606/45 X |
| 5,223,689 | 6/1993 | Cowell et al. | 219/85.22 |
| 5,242,427 | 9/1993 | Bilweis | 604/165 X |
| 5,250,036 | 10/1993 | Farivar | 604/164 |

Primary Examiner—Stephen C. Pellegrino
Assistant Examiner—M. Peffley
Attorney, Agent, or Firm—Fish & Neave; Nicola A. Pisano

[57] ABSTRACT

An irrigation arrangement is provided for electrically powered endoscopic probes that supplies the surgeon with suction or irrigation on demand. The irrigation arrangement is described for use with endoscopic probes employing thermal auto-regulating and bipolar electrosurgical probe tip configurations. An extendable shroud is also provided for selectively covering tip of the endoscopic probe while positioning or manipulating the endoscopic probe at the surgical site.

14 Claims, 6 Drawing Sheets

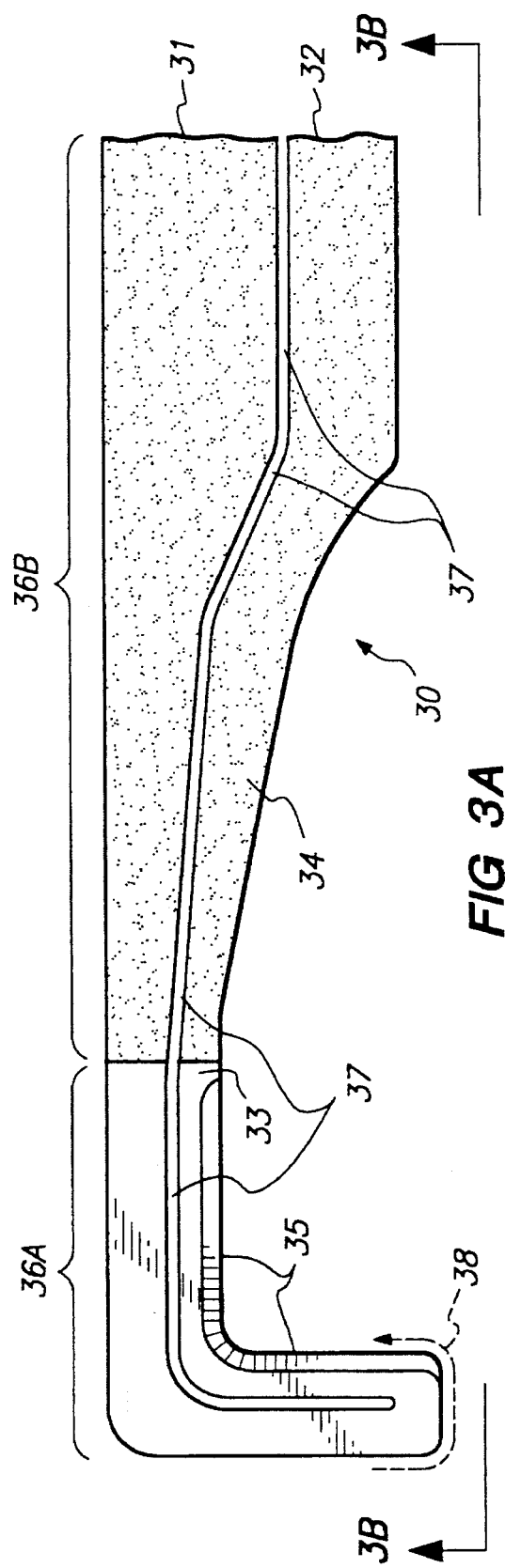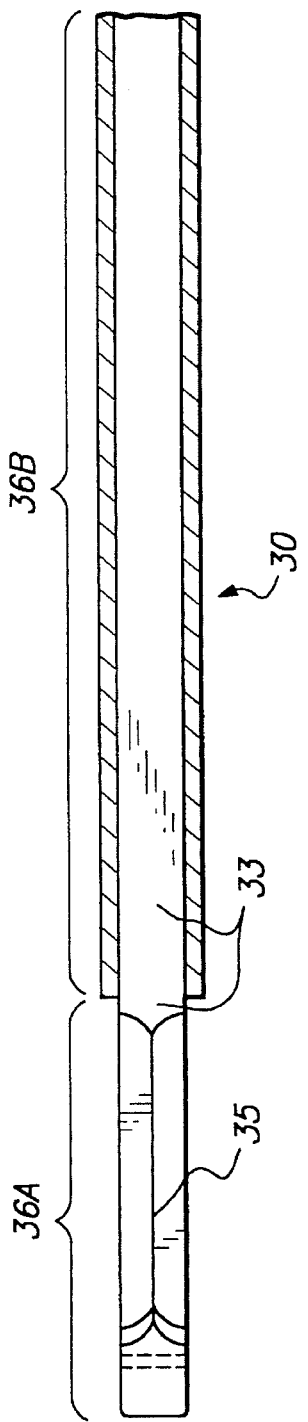

IRRIGATION AND SHROUD ARRANGEMENT FOR ELECTRICALLY POWERED ENDOSCOPIC PROBES

CROSS REFERENCES TO RELATED APPLICATIONS

This application is a continuation-in-part of commonly assigned U.S. patent application Ser. Nos. 07/877,476 filed May 1, 1992, now abandoned, and 07/959,240, filed Oct. 9, 1992.

This invention is an improvement on electrically powered endoscopic probe instruments described in the above-identified patent applications.

BACKGROUND OF THE INVENTION

Electrically powered endoscopic probes are described in and commonly assigned U.S. patent applications Ser. Nos. 877,476, filed May 1, 1992 and 07/959,240, filed Oct. 9, 1992. The devices described in those applications overcome many disadvantages inherent in previously known endoscopic probes.

The control of bleeding during surgery accounts for a major portion of the time involved in an operation. In particular, bleeding that occurs when tissue is incised or severed can obscure the surgeon's vision, prolong the operation, and adversely affect the precision of cutting. Blood loss from surgical cutting may require blood infusion, thereby increasing the risk of harm to the patient.

Controlling flow of blood from incised tissue is readily accomplished in "open" surgical procedures. The surgeon gains access to the target tissue by cutting large incisions through the body wall and displacing the overlying tissue to expose the tissue requiring treatment. A large opening is typically required to provide visibility and room to manipulate hands and instruments. Vital structures are held away from the operative site and shielded from inadvertent contact. The surgeon can directly touch and manipulate the various tissues. Bleeding from incised tissue is controlled by blotting or evacuating the accumulating blood. This step of removing the blood permits visual observation of the vessels for clamping or tying of those vessels to inhibit further blood loss.

In performing endoscopic surgery, the surgeon forgoes direct manual access to the tissue being operated upon. Consequently, traditional means of physically controlling bleeding (i.e., clamping and typing) are unavailable. Other techniques must then be employed to control bleeding during the surgical procedure. One such technique, which was first employed in "open" surgical procedures, is to thermally heat the bleeding tissue. Such thermal heating reduces the tendency of severed tissue to bleed. This process, referred to as "hemostasis," may be accomplished using either of two different endoscopic techniques to deposit sufficient heat in the tissue as described in the above-identified patent applications.

In U.S. patent application Ser. No. 07/877,476 a thermally autoregulated endoscopic probe is described, in which radio frequency electrical currents are used to maintain the working surface of the instrument at an auto-regulated temperature. The probe tip of that device comprises a heating element having a skin depth responsive to the temperature of the heating element and that decreases as the temperature of the heating element falls below the autoregulated temperature.

In my copending and commonly assigned U.S. patent application Ser. No. 07/959,240, a compact bipolar endoscopic probe is described, in which a probe blade suitable for operation at low drive voltages is provided for simultaneously cutting and cauterizing tissue. The probe blade includes a strong and flexible electrically insulative covering that reduces the possibility of losing the blade tip should undue loads cause it to fracture.

A difficulty encountered with use of the above described devices, as well as all previously known endoscopic instruments, is the inability to view the tissue as it is being cut. Despite the hemostatic action of the endoscopic probes described in the above-identified patent applications, there may nevertheless occasionally be inadvertent bleeding from a transsected vessel, the exact location of which may be difficult to identify because of the presence of active bleeding or a hematoma. Alternatively, where irrigation is provided by apparatus inserted through another cannula, the surgeon may be required to manipulate the irrigation apparatus to the site of the incision, thus creating a cumbersome arrangement of separate devices for the surgeon to control, again resulting in added effort and lost time.

It would therefore be desirable to provide irrigation apparatus to cleanse and/or evacuate the surgical site of blood and/or smoke.

It would further be desirable to provide irrigation apparatus that can be located at the surgical site with a minimum of effort and distraction to the surgeon.

SUMMARY OF THE INVENTION

In view of the foregoing, the present invention is an improvement of the electrically powered endoscopic probes described in the above-identified patent applications. It is therefore an object of this invention to provide an irrigation system for electrically powered endoscopic probes that provides the surgeon with on-demand suction or irrigation. The irrigation outlet port is located directly adjacent to the working surface of the probe, so that irrigation or evacuation can be provided on-demand as tissue is incised.

The electrically powered endoscopic probes constructed in accordance with the present invention incorporate irrigation systems within the probe shaft and handle. Controls are provided that enable the surgeon to select either irrigation or suction of the surgical site on-demand. The surgeon can therefore cleanse cut tissue, or evacuate vision-obscuring smoke simultaneously with, or immediately after, manipulating or severing the tissue, and without having to position separate irrigation apparatus at the surgical site.

In an alternative embodiment of the present invention, a two-position shroud is incorporated into the electrically powered endoscopic probe. When extended to its distal position, the shroud encircles and covers the probe tip, thereby allowing the surgeon to use the apparatus for irrigation and evacuation only, without risk of inadvertently tearing or snagging tissue with the probe tip.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which:

FIGS. 3A and 3B are, respectively, elevation and plan views of a thermally-autoregulated endoscopic probe tip similar to that of FIG. 1;

DETAILED DESCRIPTION OF THE INVENTION

Figures 1, 2:
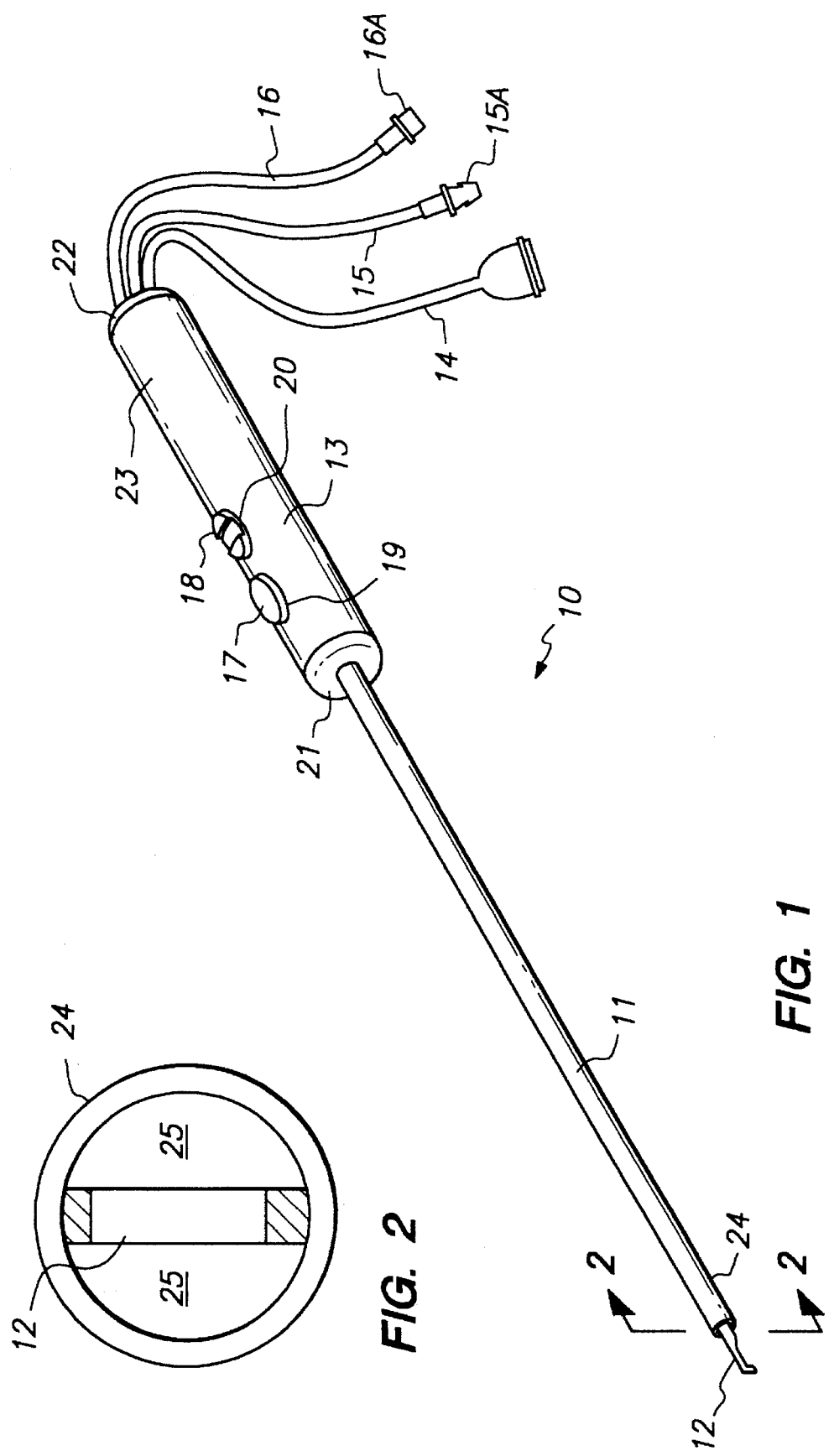
FIG. 1 is a perspective elevation view of an endoscopic probe constructed in accordance with the present invention.
FIG. 2 is an end view of the endoscopic probe of FIG. 1 taken along line 2—2 of FIG. 1.

Referring to FIG. 1, an illustrative embodiment of endoscopic probe 10 of the present invention is described. The working surface of this instrument may be used for causing hemostasis of incised tissue or for directly coagulating small tissue masses, either with or without simultaneously incising the tissue. Endoscopic probe 10 includes an elongated shaft 11 having proximal and distal ends. Elongated shaft 11 may be either flexible or rigid, depending upon the intended application. Probe tip 12 is disposed from the distal end of elongated shaft 11, while handle 13 for facilitating manipulation of the instrument is disposed from the proximal end of elongated shaft 11. Dual-wire electrical lead 14 extends from handle 13, and connects a power source (not shown) to probe tip 12 on the distal end of elongated shaft 11. As is conventional for surgical instruments, probe tip 12 of endoscopic probe 10 is electrically energized by selective actuation of a foot pedal (not shown). Suction line 15 has fitting 15A for connection to a vacuum pump (not shown), while irrigation line 16 is adapted for connection via fitting 16A to an irrigation pump (not shown). Both the vacuum pump and irrigation pumps may be conventional, and therefore form no part of the present invention. Control buttons 17 and 18 disposed through apertures 19 and 20, respectively, control selection of irrigation or suction, respectively, as described hereinafter.

Handle 13 includes front bonnet 21 and rear endcap 22 attached to the distal and proximal ends, respectively, of handle body 23. Endcap 22 includes openings that allow electrical lead 14 and suction and irrigation lines 15 and 16 to pass into the interior of handle body 23.

Distal end 24 of elongated shaft 11 includes semicircular ports 25 on either side of probe tip 12 that selectively communicate with suction line 15 and irrigation line 16. As described hereinafter, endoscopic probe 10 provides either a stream of irrigation fluid through ports 25 or suction for evacuating the region adjacent to probe tip 12 through ports 25, depending upon which of buttons 17 or 18 is depressed by the surgeon.

Thermal Auto-regulating Probe Tip

Referring now to FIGS. 3A and 3B, an endoscopic probe tip constructed in accordance with U.S. patent application Ser. No. 07/877,476 is described. Probe tip 12 may comprise heating element 30 that works as follows:

An alternating current (AC) electrical potential is applied from a power source (not shown) to terminals 31 and 32, respectively, of probe tip 12 through dual-wire electrical lead 14. In response the imposed electrical potential, an electrical current is conducted through probe tip 12. That current results in joulean heating, which raises the temperature of probe tip 12 above body temperature (i.e., approximately 37° C.) to facilitate hemostasis and optionally permit thermally-enhanced cutting of tissue.

Probe tip 12 has an auto-regulating temperature feature that results from constructing probe tip 12 of a ferromagnetic material, or other material which undergoes a similar transition in current conduction properties when the temperature of the material varies. It is known that in such materials an AC current is confined to a region adjacent the surface of the material. This phenomena is commonly called the "skin effect." The current density is generally greatest at the surface and decreases in magnitude further into the material where the electric field approaches zero. The depth at which the skin effect current is reduced to about 37 percent of its surface value is referred to as the "skin depth" and is a function of the electrical resistivity, the magnetic permeability of the material conducting the current, and the frequency of the applied alternating electric potential. It is know that the skin depth $T_{SD}$, in centimeters, can be generally represented by the equation:

$$T_{SD} = (5 \times 10^3) sqrt(rho/[uf])$$

where rho is electrical resistivity in ohm-centimeters, u is relative magnetic permeability, and f is frequency in Hertz.

Ferromagnetic materials such as iron, nickel, cobalt, and their alloys, exhibit large changes in relative permeability as the temperature goes through a transition point called the "Curie" point. Because the relative permeability changes in response to the temperature of the material, the associated skin depth also changes, and therefore the amount of current conduction through the skin layer undergoes a transition near the Curie point. This transition in current conduction properties is used to achieve auto-regulation of the temperature of probe tip 12.

An auto-regulated endoscopic probe is therefore obtained by causing a radio frequency (RF) current to flow in probe tip 12. Probe tip 12 may be composed of a ferromagnetic material or the like and uses the skin effect of the material to auto-regulate the temperature of the probe tip. Probe tip 12 is constructed of a material having a current conduction transition at or near the auto-regulation temperature desired for the particular endoscopic surgical application. When a heated portion of the working surface of probe tip 12 contacts tissue, that region of the probe tip cools below the transition temperature. In response to the local temperature drop in the probe tip, the associated skin depth responsively decreases as a result of the Curie transition in the probe tip material. The reduced skin depth in turn results in an increase in local power dissipation, so that the temperature automatically tends to increase towards the auto-regulation temperature. Accordingly, the probe tip uses the skin depth effect of the probe tip material to maintain the working surface of the endoscopic probe substantially at the auto-regulated temperature throughout the range of conditions encountered during surgery.

For example, for many iron-nickel alloys the Curie transition occurs at about 450° C., above which the relative permeability is near unity. Below about 450° C. the relative permeability is high perhaps 100 to 1000, for the magnetic field strengths suitable for use in endoscopic surgical instruments. Thus, when the local temperature of a probe tip constructed of this material falls below about 450° C., due to local cooling of the heating element when it comes into contact with cool tissue, the associated skin depth decreases more the 10 to 1. The decrease in skin depth results in an increase in local power dissipation and, thus, an increase in heating to provide auto-regulation of the probe tip temperature.

In accordance with one aspect of the present invention, probe tip 12 may be composed of a ferromagnetic material or other material which undergoes a similar transition in current conduction properties, as the temperature of the material varies through the desired auto-regulation temperature, as discussed above. Preferably, probe tip 12 is composed of an alloy of nickel and iron.

Where it is desired to operate the endoscopic instrument below the temperature range of 450°–500° C., probe tip 12 may also be coated with an electrically-insulating "non-stick" coating. Such a coating reduces the accumulation of coagulum on the working surfaces of probe tip 12 when operated at low temperatures. The application of such coatings to surgical instruments, including a description of preferred coating for the present invention, are discussed in Shaw et al. U.S. Pat. No. 4,848,337, which is incorporated herein by reference in its entirety. That patent describes an abherent coating for reducing the adherence of tissue to a surgical instrument for incising and causing hemostasis. Such coating includes materials selected from the group consisting of silicones, polydimethyisiloxanes, fluoride-metal composites nd fluorocarbon polymers.

If a non-stick coating is desired, the coating may, more preferably, be either a fluorine-containing mixture, such as polytetrafluoroethylene (PTFE), of a fluorotelomer-based mixture. In particular, the coating may be either of type XYLAN® 8110/870 Black, available from Whitford Corporation of West Chester Pa., which is PTFE-based, or type VYDAX® 1000 FLUOROTELEMER DISPERSION, available from E. I. du Pont de Nemours & Co., Inc., of Wilmington, Del., which is a fluorotelomer based-mixture. VYDAX® is preferred for longer-lasting applications where the surgical instrument will be reused multiple times. Furthermore, the VYDAX® thickness should preferably be in the range of approximately 0.3 to 0.4 mil (0.0075 to 0.01 mm).

Probe tip 12 shown in FIG. 3 comprises monolithic heating element 30. Heating element 30 includes auto-regulating substrate 33, overlayer 34 and optional taper 35. Auto-regulating metal substrate 33 comprises a ferromagnetic material, or other material which undergoes a similar transition in current conduction properties, when the temperature of the material varies. Auto-regulating metal substrate 33 has a high-temperature working surface region 36a and a low-temperature region 36b. An AC electric potential placed across terminals 31 and 32 in low-temperature region 36b causes an AC electric current to flow between terminals 31 and 32 and thus, through high-temperature working surface region 36a. Terminals 31 and 32 are separated by an isolation air gap 37, which electrically isolates terminal 31 from 32, and which forces the AC current flowing through heating element 30 to conduct around loop 38 in high-temperature working surface region 36a. Isolation air gap 37 may be filled with alumina cement or other similar material to provide a smooth easy-to-clean surface. The AC current is conducted within the skin-depth of substrate 33 in high-temperature working surface region 36a and around loop 38.

The resulting power dissipation heats region 36a to high temperatures sufficient to cause hemostasis of tissue and, if desired, thermally-enhanced cutting of the tissue. Auto-regulation of the temperature of high-temperature working surface region 36a is achieved by constructing region 36a of auto-regulating metal, such as a ferromagnetic metal or the like.

Low-temperature region 36b of substrate 33 is covered with overlayer 34, a material that confines the heat generated in high-temperature working surface region 36a to the working surface area of the endoscopic instrument. Overlayer 34 may comprise a nonferromagnetic metal or alloy comprised of nickel or copper, and which has a low thermal conductance, and thus stays at relatively low temperatures compared to region 36a.

Other features of the thermally auto-regulated probe tip 12 of the present invention may be obtained from copending U.S. patent application Ser. No. 07/877,476, the specification and drawings of which are incorporated herein by reference in their entirety.

Bipolar Endoscopic Probe Tip

Figure 4A:
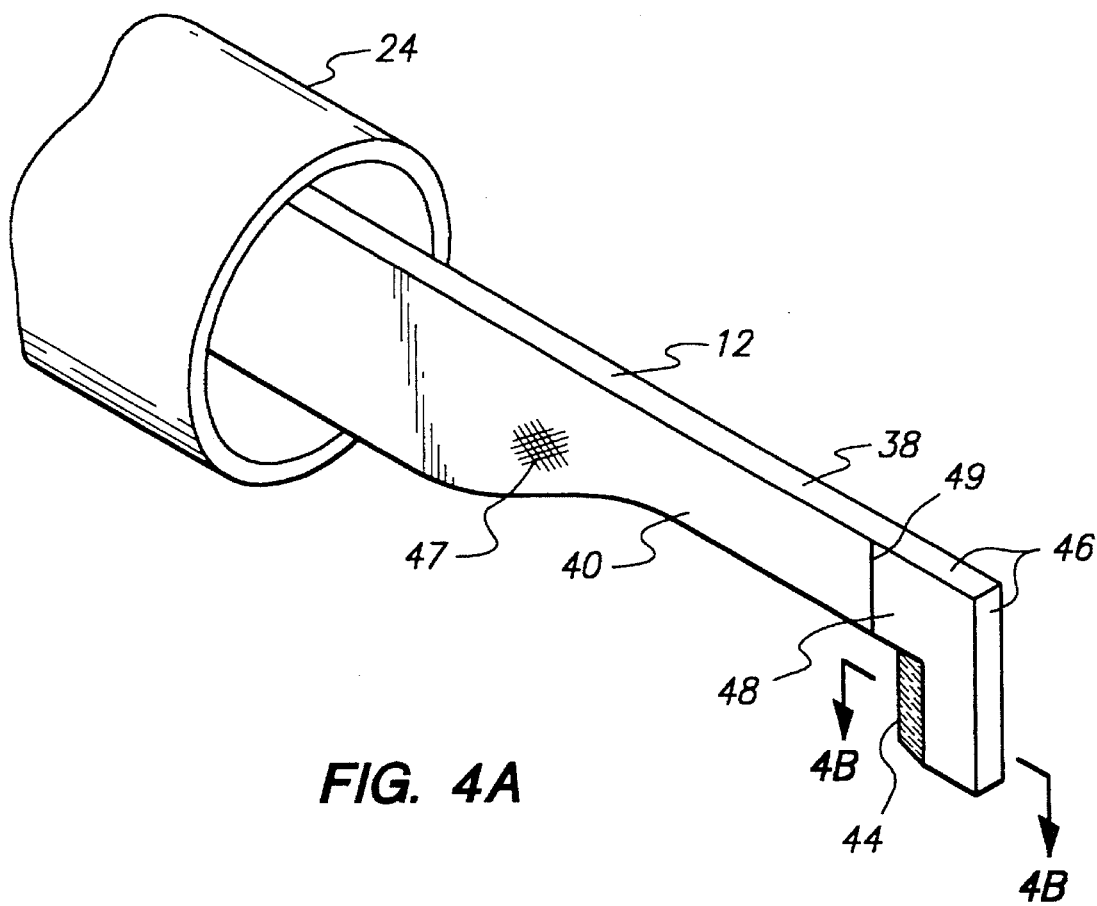
FIG. 4A is a perspective view of a bipolar endoscopic probe tip similar to that of FIG. 1.
Figure 4B:
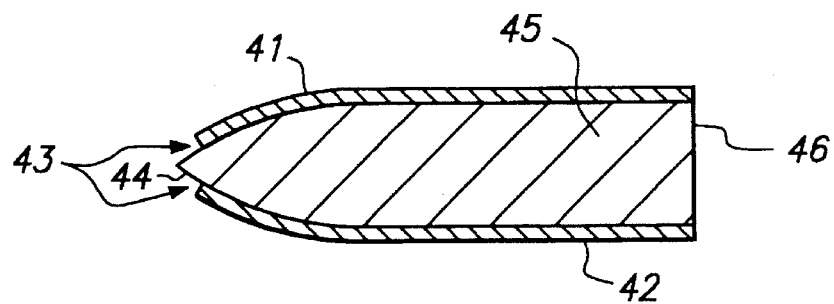
FIG. 4B is a cross-sectional view of the bipolar endoscopic probe tip of FIG. 4A taken along the line 4B—4B of FIG. 4A.

Referring now to FIGS. 4A and 4B, an endoscopic probe tip constructed in accordance with my copending U.S. patent application Ser. No. 07/959,240, filed Oct. 9, 1992, is described.

Probe tip 12 comprises working end 40 having bipolar electrodes formed thereon. Working end 40 applies current to tissue through electrodes 41 and 42, which are separated by gap 43 at blade tip 44. This gap is preferably from 0.1 mm to 1 mm in length, which spans the circumference around blade tip 44 from the end of electrode 41 to electrode 42. When a drive signal is applied across electrodes 41 and 42, an electric field is created in the vicinity of blade tip 44. For example, if the drive voltage has a magnitude of 50 V and the gap size is 0.5 mm, an electric field of $10^3$ V-cm$^{-1}$ is produced. Due to the influence of this electric field, tissue in contact with electrodes 41 and 42 conducts current. The current flow weakens the tissue and the resulting ohmic heating cauterizes the tissue. The weakened tissue is effectively cut by blade tip 44. With a probe blade constructed in accordance with the present invention, the unenergized probe tip may be inserted into the body with minimal injury to normal tissue. When the probe is disposed at the surgical site, it may be energized so that the sharpness of the blade is enhanced.

The electric fields generated between electrodes 41 and 42 are preferably too low to cause current arcing between the electrodes. However, the probe must still be constructed to withstand possible electrical damage. Accordingly, substrate 45 of working end 40 is constructed from a durable insulator such as zirconia. In a preferred embodiment zirconia material No. A701N from Kyocera Corporation of S-22 Kitainoue-cho, Higashino, Yamashina-ku, Kyoto 67, Japan is isostatically hot pressed into the desired probe tip shape. The probe tip can further be shaped by grinding, for instance, to form the blade region.

Working end 40 is connected to the power supply by wires that pass through elongated shaft 11, handle 13, and electrical lead 14. Electrodes 41 and 42 are formed by conductive metallic layers that are deposited on the lateral faces of substrate 45 using conventional techniques such as evaporation or sputtering. These conductive metallic layers are not deposited on the other surfaces of working end 40 such as surfaces 46. Electrodes 41 and 42 are preferably formed primarily of a highly conductive metal such as silver. In order to enhance adhesion of the conductive metal to working end 40, an adhesion layer of, for example, titanium, may first be deposited on the probe tip. Additionally, following the deposition of the silver layer a protective layer of a suitable bioactively inert metal such as platinum may be deposited in order to encapsulate the silver layer. The protective layer prevents oxidation of the silver layer and also provides a stable coating that may be more resistant to the sticking of coagulum and tissue to the blade portion of working end 40. In one preferred embodiment, the titanium layer is 0.25 μm thick, the silver layer is 1.5 μm thick and the platinum layer is 0.5 μm thick.

In accordance with another aspect of the present invention, if desired, electrodes 41 and 42 may also be coated with an electrically-conducting "non-stick" or abherent coating. Such a coating reduces accumulation of coagulum on the surface of the blade. The non-stick coating should provide an intimate contact with the surface of electrodes 41 and 42 but not significantly impede electrical current flow through the protruding tissue. Further, if a non-stick coating is applied to electrodes 41 and 42, it should not allow the electrodes to electrically short together. Thus, the non-stick coating material should not be provided in regions such as gap 43 at blade tip 44 or other similar regions where shorting between electrodes may occur if there is a continuous path of electrically conducting non-stick coating. Masking, selective removal steps, or other conventional techniques can be used to selectively provide the non-stick coating in desired regions and thereby prevent shorting of the electrodes.

If a non-stick coating is desired, its thickness should preferably be in the range of approximately 0.2 to 2 μm. One suitable coating is the fluorotelemer dispersion sold under the trademark "VYDAX 1000", owned by E. I. du Pont and de Nemours & Company of Wilmington, Del., as described heretofore. Preferably, the active (exposed) portions of electrodes 41 and 42 are coated with this film, which is electrically conducting, and which minimizes sticking of the blade edge adjacent to electrodes 41 and 42 to tissue.

As shown in the illustrative embodiment of FIGS. 4A and 4B, film 47 covers most of the conductive layer on the lateral faces of working end 40, but does not cover region 48, or electrodes 41 or 42. In FIG. 4A, the border between film 47 and region 48 is defined by line 49. If it is desired to extend the film further, film 47 can be extended to cover the flat surfaces of working end 40 in region 48.

Film 47 is preferably a strong adhesive-backed flexible electrically insulating film, preferably a polyimide film (such as the polyimide commonly known under the trademark Kapton owned by E. I. du Pont and de Nemours & Company). Film 47 not only insulates working end 40, but also maintains the structural integrity of the probe tip in the event of an accidental fracture of the probe tip during surgery. Such breakage could result in the undesirable loss of a portion of working end 40 within the patient's body. When film 47 is attached to working end 40, even if a break occurs and probe 10 becomes inoperable, film 47 continues to retain the broken portion of the probe tip attached to the probe so that the broken piece can be removed from the body.

Other features of bipolar probe tip 12 of the present invention may be obtained from concurrently filed U.S. patent application Ser. No. 07/959,240, the specification and drawings of which are incorporated herein by reference in their entirety.

Endoscopic Probe Irrigation Arrangement

Figure 5:
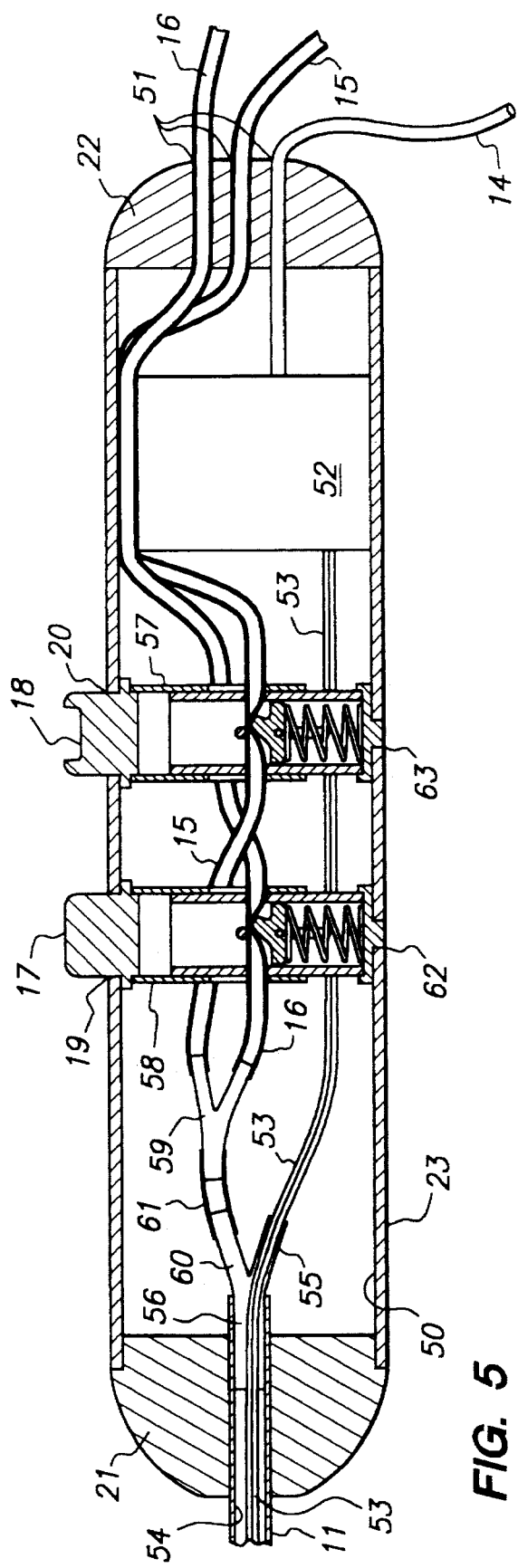
FIG. 5 is a cross-sectional view of the internal components of a handle constructed in accordance with the present invention, taken along line 5—5 of FIG. 1.
Figure 6:
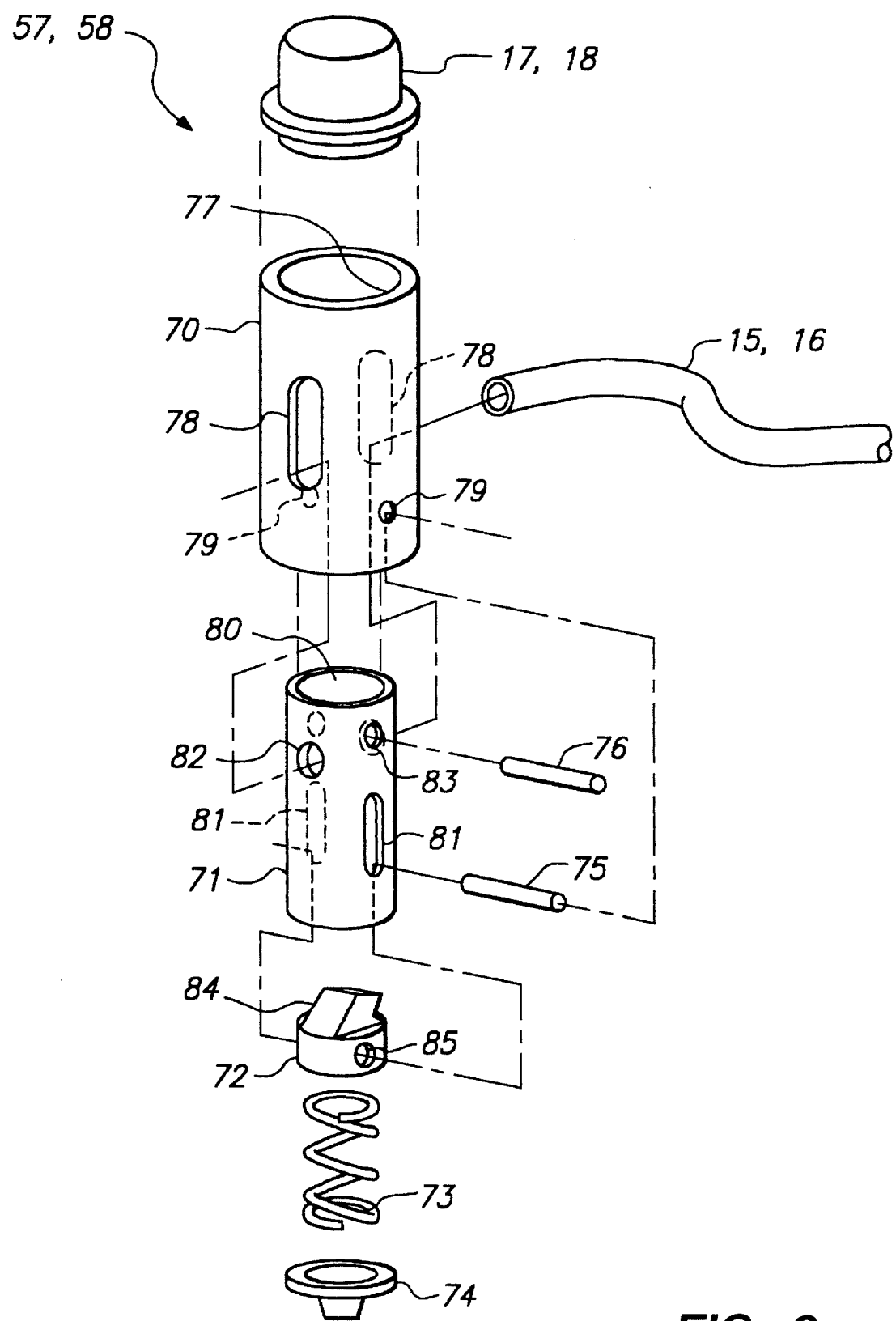
FIG. 6 is an exploded perspective view of an irrigation system control valve assembly shown in FIG. 5.

Referring now to FIGS. 1, 5 and 6, the internal components of the endoscopic probe irrigation arrangement of the present invention are described. Shown in FIG. 5 are the front bonnet 21, handle body 23 and rear endcap 22. Handle body 23 includes interior cavity 50. Elongated shaft 11 is shown secured in front bonnet 21 by conventional means, such as epoxy or other conventional fastener such as pins or screws (not shown). Likewise dual-wire electrical lead 14, suction line 15, and irrigation line 16 are shown entering into interior cavity 50 through bores 51 in rear endcap 22. Control buttons 17 and 18 extend through apertures 19 and 20, respectively, in handle body 23.

As shown in FIG. 5, dual-wire electrical lead 14 passes through bore 51 and connects to transformer 52. Transformer 52 may be used in conjunction with a thermal auto-regulating probe tip as described hereinabove, or deleted if a bipolar endoscopic probe tip, as described hereinabove, is to be used. Lead 53 connects transformer 52 (or lead 14, if transformer 52 is not present) to probe tip 12. Lead 53 enters into bore 54 of elongated shaft 11 through leg 55 of Y-shaped connector 56. Lead 53 runs the full length of bore 54 and connects to probe tip 12. A leak-proof seal is provided where lead 53 enters leg 55 using a conventional sealant such as an epoxy. As would be understood by one skilled in the art, lead 53 is covered with an electrically insulating material, as is the junction (not shown) between lead 53 and probe tip 12.

Control buttons 17 and 18 are seated atop control valve assemblies 57 and 58. Control button 17 has a domed top, while control button 18 has a concave top, so that the surgeon can differentiate between the buttons without looking at them. Suction line 15 is routed around transformer 52 (if present) and passes through control valve assembly 57, while irrigation line 16 is similarly routed and passes through control valve assembly 58. Suction line 15 and irrigation line 16 comprise flexible and resilient tubing, for example, silicon tubing. Suction line 15 and irrigation line 16 terminate at Y-shaped connector 59. The outlet of Y-shaped connector 59 is in turn connected to leg 60 of Y-shaped connector 56 by silicon tubing 61. Thus, by actuating either control buttons 17 or 18, either irrigation or suction, respectively, is provided to bore 54 of elongated shaft 11. This suction or irrigation is transmitted through bore 54 to distal end 24 of elongated shaft 11, where it is manifested at ports 25 (see FIG. 2).

Control valve assemblies 57 and 58 are secured in position in handle body 23 by control buttons 17 and 18 at the top of the assemblies and by protrusions extending from the bottoms of the control valve assemblies into apertures 62 and 63 in handle body 23. Control valve assemblies 57 and 58 are essentially identical, except for the configuration of the control button, i.e., either domed or concave, and the line passing through the assembly, i.e., either suction line 15 or irrigation line 16.

As shown in FIG. 6, each control valve assembly comprises outer sleeve 70, inner sleeve 71, plunger 72, spring 73, platen 74, pins 75 and 76, and control button 17 or 18. Control button 17 or 18, outer sleeve 70, inner sleeve 71, plunger 72, platen 74 and pins 75 and 76 are formed of a sturdy light-weight material, for example, aluminum. Outer sleeve 70 has central bore 77, in which inner sleeve 71 is slidably disposed. Outer sleeve 70 includes diametrically opposed elongated slots 78 and diametrically opposed holes 79. Elongated slots 78 have a width slightly greater than that of suction or irrigation lines 15 or 16 and a length at least twice that size, so that lines 15 or 16 can move freely in elongated slots 78. Holes 79 engage the ends of pin 75, as described below.

Inner sleeve 71 includes central bore 80, diametrically opposed elongated slots 81, diametrically opposed tubing holes 82, and diametrically opposed holes 83. Elongated slots 81 are dimensioned to accept pin 75 so as to permit it to move freely along elongated slots 81. Tubing holes 82 permit either suction line 15 or irrigation line 16 to pass therethrough. Holes 83 retain the ends of pin 76, which extends across bore 80 of inner sleeve 71 to provide an anvil against which plunger 72 urges suction or irrigation lines 15 or 16.

Plunger 72 comprises an aluminum disk having an upwardly extending ridge 84 that collapses the tubing of suction line 15 or irrigation line 16 against pin 76. Plunger 72 includes bore 85 for accepting pin 75. Platen 74 retains the control valve assembly in position in handle body 23 by engaging apertures 62 or 63, while spring 73 biases plunger 72 against suction line 15 or irrigation line 16.

As shown by the dotted lines in FIG. 6, control valve assembly 57 or 58 is assembled as follows: inner sleeve 71 is slidably disposed within outer sleeve 72, and the flexible tubing forming suction line 15 or irrigation line 17 passes through elongated slots 78 of outer sleeve 70 and tubing holes 82 of inner sleeve 71. Pin 76 is fixed in holes 83 of inner sleeve 71, for example by peening, so that it does not interfere with the relative motion of outer sleeve 70 over inner sleeve 71. Pin 76 passes directly above the top of suction line 15 or irrigation line 16, and therefore serves as an anvil for plunger 72.

Plunger 72 is slidably disposed in bore 80 of inner sleeve 71 by pin 75, which extends through holes 79 in outer sleeve 70, through elongated slots 81 in inner sleeve 71, and through bore 85 in plunger 72. Thus, plunger is fixed relative to outer sleeve 70 by pin 75, but is capable of vertical travel in inner sleeve 71 as pin 75 rides in elongated slots 81. Spring 73, which may be a conventional steel spring, is captured in bore 80 of inner sleeve 71 between platen 74 and plunger 72.

It therefore follows from the foregoing arrangement of elements that spring 73 biases plunger 72 (and therefore outer sleeve 70 via pin 75) upwards so that the flexible tubing comprising suction line 15 or irrigation line 16 is collapsed between pin 76 and ridge 84 of plunger 72. Thus, when button 17 or 18 is depressed, outer sleeve 70 moves downward, carrying pin 75 and plunger 72 with it. During this downward motion, suction line 15 or irrigation line 16 rides in elongated slots 78 of outer sleeve 70, while the portion of the suction or irrigation line extending through tubing holes 82 of inner sleeve 71 remains stationary. Consequently, when ridge 84 of plunger 72 is moved out of contact with the flexible tubing of suction line 15 or irrigation line 16, the tubing assumes its circular cross-section, thereby enabling irrigation fluid or suction to be transmitted to leg 60 of Y-shaped connector 55.

As will be further understood from the foregoing description, control valve assemblies 57 and 58 are biased closed, while enabling the surgeon to provide suction or irrigation to ports 25 on-demand by depressing either control button 17 or 18. A further advantage in irrigation using the present arrangement may be realized by employing an irrigation pump that provides a pulsating fluid stream. The use of a pulsating fluid stream serves to cleanse the surgical site while enabling inspection of the site between introduction of the bursts of fluid. If a pulsating fluid stream, which may be obtained from a conventional irrigation pump, is used, care must be taken in selecting the stiffness of spring 73 sufficiently high so that plunger 72 is not inadvertently opened by the pressure pulses in the irrigation fluid induced by the irrigation pump.

Figure 8:
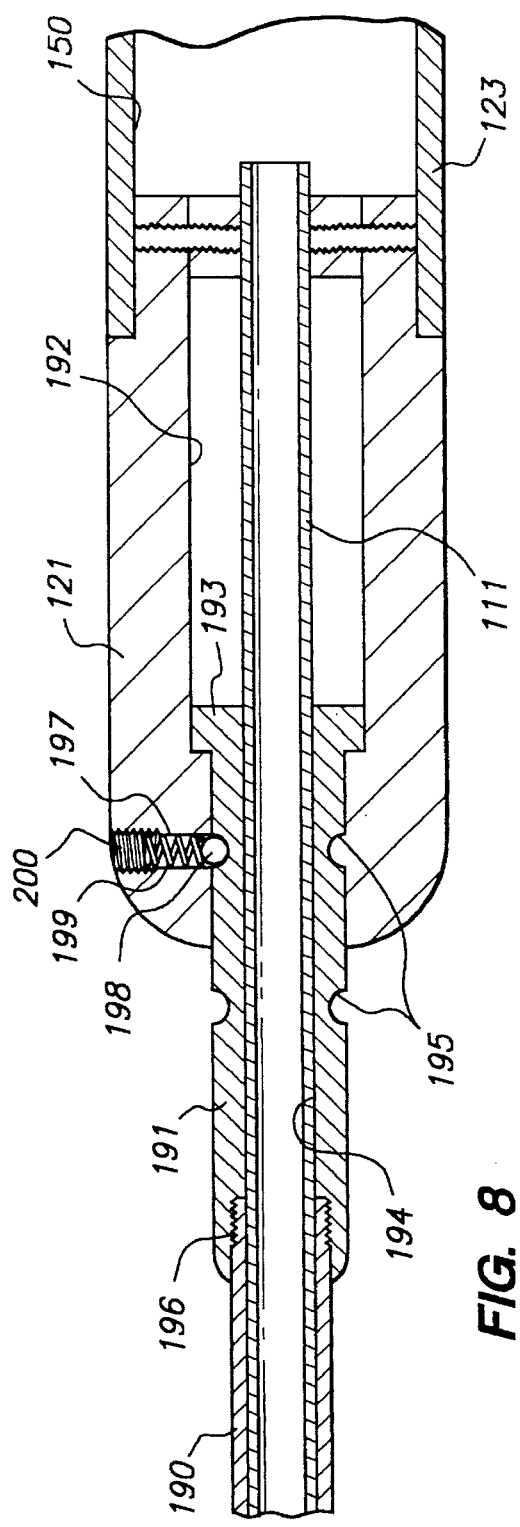
FIG. 8 is a cross-sectional view of the endoscopic probe of FIG. 7 taken along line 8—8 of FIG. 7.
Figure 7:
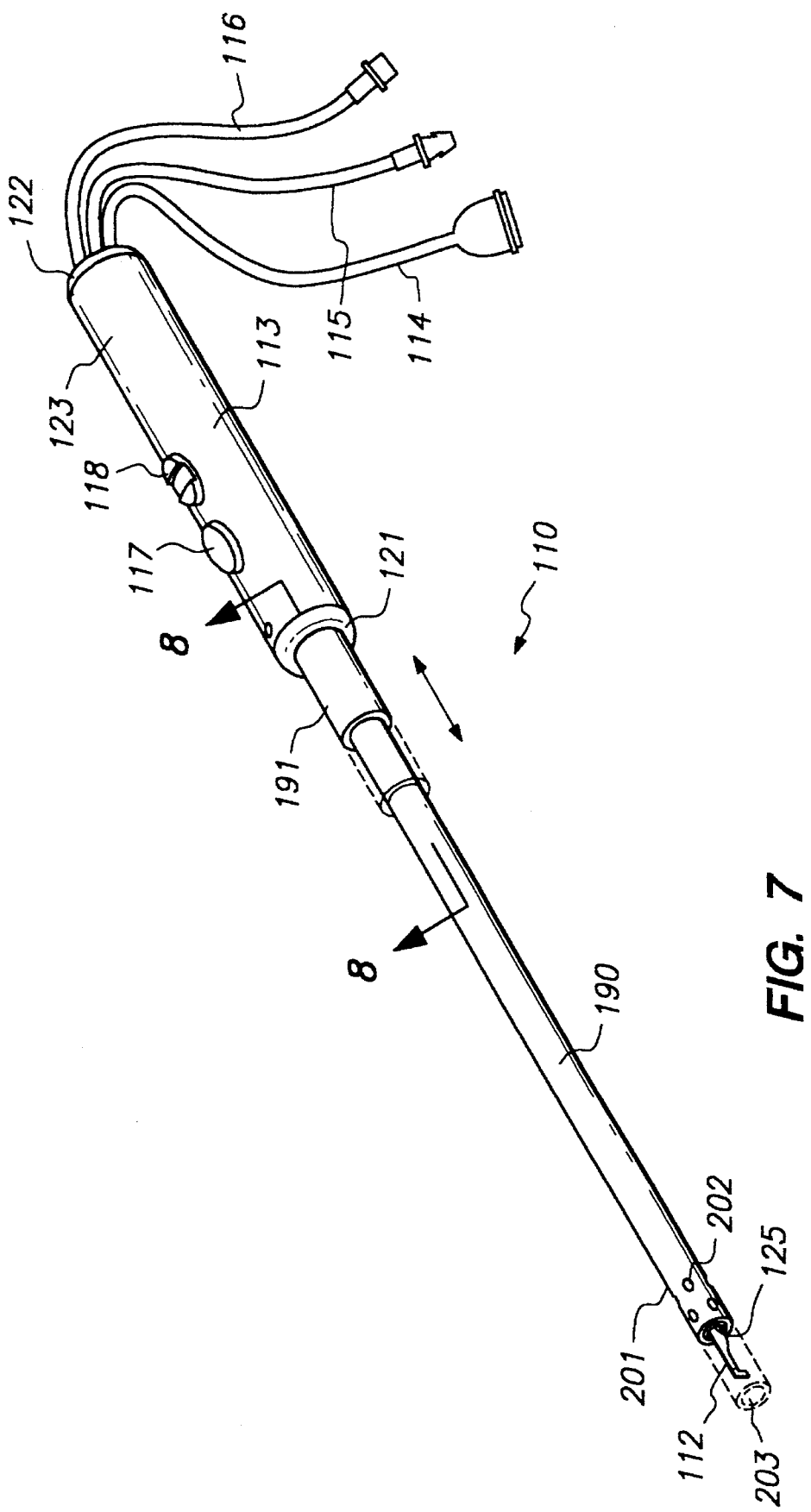
FIG. 7 is an alternative embodiment of an endoscopic probe of the present invention incorporating an extendable shroud.

Referring now to FIGS. 7 and 8, endoscopic probe 110 having extendable shroud 190 is described. Parts of endoscopic probe 110 that are like parts of endoscopic probe 10 described heretofore, are identified by like numbers increased by 100. For example, the control buttons of endoscopic probe 110 are constructed as described above and are identified as 117 and 118.

Endoscopic probe 110 includes tubular shroud 190 slidably disposed on elongated shaft 111, and indexing sleeve 191. As shown in FIG. 7, indexing sleeve may be extended from front bonnet 121 so that tubular shroud 190 extends in the distal direction to encircle and cover probe tip 112. When shroud 190 is extended the surgeon may freely position and manipulate instrument 110 at the surgical site to provide suction or irrigation without concern that probe tip 112 might inadvertently snag or cut the tissue. Alternatively, the surgeon may choose to use instrument 110 as an auxiliary suction or irrigation instrument where he is using several other endoscopic instruments at the surgical site.

Distal end 201 of tubular shroud 191 includes eight holes 202 about 1.5 mm in diameter arranged about distal end 201, in two rows having 4 holes spaced equidistant apart about the circumference of distal end 201. The first row of holes is spaced a distance equal to about one diameter of tubular shroud 191 from end 203 of tubular shroud 191, with the second row, which is offset about 45° from the first row, set about the same distance in the proximal direction from the first row. Holes 202 facilitate suction through the distal end 201 of tubular shroud 191 when it is extended to its distal position, by preventing tissue at the surgical site from being drawn into the bore in end 203 of the shroud by the suction induced through ports 125. In addition, end 203 of tubular shroud 191 is sanded or ground to remove sharp edges that might injure tissue if tissue were to become engaged in end 203.

In FIG. 8 the electrical lead wire, Y-connectors and other internal components have been omitted for clarity, although those components are to be understood to be present as shown in FIG. 5. Front bonnet 121 includes an internal compartment 192 dimensioned to accept flange 193 of indexing sleeve 191. Indexing sleeve 191 is machined out of a sturdy material, for example aluminum, to have flange 193, central bore 194 and two semicircular grooves 195. Indexing sleeve 191 includes portion 196 at its distal end for accepting tubular shroud 190, which is affixed to indexing sleeve 191 by conventional means, such as threads, or heat shrinkable tubing. Indexing sleeve 191 is slidably disposed on elongated shaft 111 for movement in the proximal and distal directions when the region of indexing sleeve 191 extending from front bonnet 121 is grasped by the surgeon.

Front bonnet 121 includes threaded bore 197 in which ball 198, spring 199, and capnut 200 are disposed. Ball 198 is biased against the exterior of indexing sleeve 191 by spring 199. Spring-loaded ball 198 seats in semicircular grooves 195 when indexing sleeve is translated between its retracted and extended positions (extended position shown in FIG. 8 and in phantom lines in FIG. 7), thereby retaining the indexing sleeve in the desired position. Spring-loaded ball 198 engages grooves 195 with adequate force to prevent unintended movement of indexing sleeve 191 during manipulation at the surgical site, but allows the surgeon to extend or retract shroud 190 by grasping indexing sleeve 191 and urging it in the distal or proximal directions with sufficient force.

As will be readily understood by one skilled in the art, the extendable shroud aspect of the irrigation arrangement of the present invention may be incorporated into either of the endoscopic probes described heretofore.

One skilled in the art will appreciate that the present invention can be practiced by other than the described embodiments, which are presented for purposes of illustration and not of limitation, and the present invention is limited only by the claims that follow.

What is claimed is:

1. An instrument for use in endoscopic surgery, the instrument connected to a suction source, an irrigation source, and a power source, the instrument comprising:

an elongated shaft having a proximal end, a distal end, and a central bore;

an electrically powered probe tip connected to the distal end of the elongated shaft;

means for connecting the electrically powered probe tip to the power source;

a handle connected to the proximal end of the elongated shaft, the handle having a first passageway for transmitting suction from the suction source to the central bore, and a second passageway for transmitting irrigation from the irrigation source to the central bore; and valve means disposed in the first and second passageways for biasing the first and second passageways closed, the valve means enabling either of the first and second passageways to be selectively opened, wherein the electrically powered probe tip comprises a working end disposed from the distal end of the elongated shaft, the working end having a cross-section extending perpendicularly to the working surface, the working surface maintained at an auto-regulated temperature by conducting a current throughout the cross-section of the working end, the heating element comprising a material having a skin depth extending substantially throughout the cross-section of the working end responsive to the temperature of the heating element and that decreases as the temperature of the element falls below the auto-regulated temperature.

2. An instrument as defined in claim 1 wherein the material of said heating element further comprises a material that exhibits a curie transition in permeability.

3. An instrument as defined in claim 2 wherein the material further comprises a ferromagnetic material.

4. An instrument as defined in claim 1 wherein the working surface further comprises a coating of electrically-insulating non-stick material to reduce the accumulation of coagulum on the working surface.

5. An instrument as defined in claim 1 wherein the valve means comprises first and second control valve assemblies, the first and second control valve assemblies each comprising:

a plunger;

a control button; and biasing means for biasing the plunger to close one of the first and second passageways, the biasing means responsive to the control button to selectively open one of the first and second passageways.

6. An instrument as defined in claim 1 further comprising:

a tubular shroud slidably disposed on the elongated shaft, the tubular shroud having a distal end;

an indexing sleeve slidably disposed on the elongated shaft, the indexing sleeve fixedly connected to the tubular shroud, the indexing sleeve movable between a distal position wherein the distal end of the tubular shroud encircles and covers the probe tip and a proximal position wherein the distal end of the tubular shroud uncovers the probe tip; and means for retaining the indexing sleeve in the distal and proximal positions.

7. An instrument as defined in claim 1 wherein the control button of the first control valve assembly is shaped differently than the control button of the second control valve assembly, so that the operator can distinguish the first control valve assembly from the second control valve assembly by touch.

8. An instrument for use in endoscopic surgery, the instrument connected to a suction source, an irrigation source, and a power source, the instrument comprising:

an elongated shaft having a proximal end, a distal end, and a central bore;

an electrically powered probe tip connected to the distal end of the elongated shaft;

means for connecting the electrically powered probe tip to the power source;

a handle connected to the proximal end of the elongated shaft, the handle having a first passageway for transmitting suction from the suction source to the central bore, and a second passageway for transmitting irrigation from the irrigation source to the central bore; and valve means disposed in the first and second passageways for biasing the first and second passageways closed, the valve means enabling either of the first and second passageways to be selectively opened, wherein the electrically powered probe tip comprises a substrate having a portion defining a cutting edge, the cutting edge having first and second lateral faces, the cutting edge being insufficiently sharp to cut tissue in the absence of electric current;

a first electrode formed on the first lateral face, the first electrode having an edge adjacent the cutting edge;

a second electrode formed on the second lateral face, the second electrode having an edge adjacent the cutting edge, so that the distance from the edge of the first electrode to the edge of the second electrode defines a gap, so that electric current flows between the first and second electrodes across the gap without arcing, and the cutting edge becomes acquires an enhanced sharpness when electric current flows across the gap; and a flexible film covering the first and second lateral faces of the probe tip for securing to the probe a portion of the probe tip should the probe tip fracture during surgery.

9. An instrument as defined in claim 8 wherein the substrate comprises an electrically insulating material and the first and second electrodes comprise metallic layers disposed on the first and second lateral faces.

10. An instrument as defined in claim 9 wherein the gap is in the range of from 0.1 mm to 1.0 mm.

11. An instrument as defined in claim 8 wherein the flexible film is an electrically insulating film disposed on a portion of the first and second electrodes for providing electrical insulation of the first and second electrodes remote from the cutting edge.

12. An instrument as defined in claim 8 wherein the valve means comprises first and second control valve assemblies, the first and second control valve assembles each comprising:

a plunger;

a control button; and biasing means for biasing the plunger to close one of the first and second passageways, the biasing means responsive to the control button to selectively open one of the first and seconds passageways.

13. An instrument as defined in claim 8 further comprising:

a tubular shroud slidably disposed on the elongated shaft, the tubular shroud having a distal end;

an indexing sleeve slidable disposed on the elongated shaft, the indexing sleeve fixedly connected to the tubular shroud, the indexing sleeve movable between a distal position wherein the distal end of the tubular shroud encircles and covers the probe tip and a proximal position wherein the distal end of the tubular shroud uncovers the probe tip; and means for retaining the indexing sleeve in the distal and proximal positions.

14. An instrument as defined in claim 8 wherein the control button of the first control valve assembly is shaped differently than the control button of the second control valve assembly, so that the operator can distinguish the first control valve assembly from the second control valve assembly by touch.

* * * * *